United States Patent
Zhao et al.

(10) Patent No.: US 12,280,077 B2
(45) Date of Patent: Apr. 22, 2025

(54) BIFIDOBACTERIUM LONGUM WITH THE ABILITY TO RELIEVE ATOPIC DERMATITIS AND ITS APPLICATION

(71) Applicant: Jiangnan University, Wuxi (CN)

(72) Inventors: Jianxin Zhao, Wuxi (CN); Wenwei Lu, Wuxi (CN); Wei Chen, Wuxi (CN); Zhifeng Fang, Wuxi (CN); Qixiao Zhai, Wuxi (CN); Bo Yang, Wuxi (CN); Hao Zhang, Wuxi (CN)

(73) Assignee: Jiangnan University, Wuxi (CN)

( * ) Notice: Subject to any disclaimer, the term of this patent is extended or adjusted under 35 U.S.C. 154(b) by 803 days.

(21) Appl. No.: 17/325,280

(22) Filed: May 20, 2021

(65) Prior Publication Data

US 2021/0268043 A1   Sep. 2, 2021

Related U.S. Application Data

(63) Continuation of application No. PCT/CN2019/128526, filed on Dec. 26, 2019.

(30) Foreign Application Priority Data

Feb. 25, 2019   (CN) .......................... 201910137571.2

(51) Int. Cl.
    *A61K 35/745*    (2015.01)
    *A23L 33/135*    (2016.01)
    (Continued)

(52) U.S. Cl.
    CPC .......... *A61K 35/745* (2013.01); *A23L 33/135* (2016.08); *C12N 1/205* (2021.05);
    (Continued)

(58) Field of Classification Search
    None
    See application file for complete search history.

(56) References Cited

U.S. PATENT DOCUMENTS

11,337,926 B2 *   5/2022   Zhang ................... A61K 9/2054
2018/0289754 A1 *  10/2018   Rosignoli ................ A61K 9/06

FOREIGN PATENT DOCUMENTS

| CN | 102089422 A | 6/2011 |
| CN | 102159086 A | 8/2011 |

(Continued)

OTHER PUBLICATIONS

Abe, F; et al; "Effect of production conditions on the stability of a human *Bifidobacterial* species *Bifidobacterium longum* in yogurt" Letters in Applied Microbiology, 49, 715-720, 2009 (Year: 2009).*

(Continued)

*Primary Examiner* — David W Berke-Schlessel
(74) *Attorney, Agent, or Firm* — IPRO, PLLC; Na Xu

(57) ABSTRACT

The disclosure discloses *Bifidobacterium longum* with the ability to relieve atopic dermatitis and its application, and belongs to the technical fields of microorganisms and medicine. The *Bifidobacterium longum* of the disclosure has the effects of relieving atopic dermatitis, and the effects are specifically embodied in: (1) significantly improving the degree of ear swelling in mice with atopic dermatitis; (2) significantly improving skin pathological symptoms and inflammatory cell infiltration in mice with atopic dermatitis; (3) significantly reducing the serum IgE level in mice with atopic dermatitis; (4) significantly reducing the levels of IL-4 and IL-13 in the skin tissues of mice with atopic dermatitis; and (5) significantly reducing the level of histamine in the skin tissues of mice with atopic dermatitis. Therefore, the *Bifidobacterium longum* has great application prospects in the preparation of products for the prevention and/or treatment of atopic dermatitis.

13 Claims, 4 Drawing Sheets

Specification includes a Sequence Listing.

(51) Int. Cl.
*C12N 1/20* (2006.01)
*C12R 1/01* (2006.01)

(52) U.S. Cl.
CPC ...... *C12N 2500/34* (2013.01); *C12N 2500/46* (2013.01); *C12N 2500/74* (2013.01); *C12N 2523/00* (2013.01); *C12R 2001/01* (2021.05)

(56) References Cited

FOREIGN PATENT DOCUMENTS

| CN | 107567333 A | 1/2018 | |
|---|---|---|---|
| CN | 108473944 A | 8/2018 | |
| CN | 108495560 A | 9/2018 | |
| CN | 109652349 A | 4/2019 | |
| EP | 3272396 A1 * | 1/2018 | ........... A23L 33/135 |
| KR | 20180089324 A | 8/2018 | |
| WO | 2010003916 A1 | 1/2010 | |
| WO | 2016149687 A1 | 9/2016 | |

OTHER PUBLICATIONS

Sakata, Shinji; et al; "Unification of *Bifidobacterium infantis* and *Bifidobacterium suis* as *Bifidobacterium longum*" International Journal of Systematic and Evolutionary Microbiology, 52, 1945-1951, 2002 (Year: 2002).*

Fang, ZF et al., "Strain-specific ameliorating effect of *Bifidobacterium longum* on atopic dermatitis in mice" Journal of Functional Foods, Jun. 21, 2019. vol. 60-103426.

Yang J et. al., "*Bifidobacterium longum* BBMN68-specific modulated dendritic dcells alleviate allergic responses to bovine beta-lactoglobulin in mice", Journal of Applied Microbiology, Aug. 6, 2015, vol. 4, Iss 119, p. 1127-1137.

* cited by examiner

BIFIDOBACTERIUM LONGUM WITH THE ABILITY TO RELIEVE ATOPIC DERMATITIS AND ITS APPLICATION

TECHNICAL FIELD

The disclosure relates to *Bifidobacterium longum* with the ability to relieve atopic dermatitis and its application, and belongs to the technical fields of microorganisms and medicine.

BACKGROUND

Atopic Dermatitis (AD) is a chronic, recurrent, inflammatory skin disease, which is often accompanied by severe itching and other allergic diseases. At the same time, AD is a common non-communicable skin disease, affecting up to 20% of children and 2-8% of adults in most countries around the world (Wollenberg A et al., 2018). The clinical manifestations of AD are diversified. According to occurrence, development and distribution characteristics, AD can be divided into three stages: infancy, childhood, adolescence and adulthood. Among them, most AD patients occur in infancy, and those with severe conditions can even continue to adulthood. Since the quality of life of patients is seriously affected due to its repetitiveness, AD is one of the world's public health problems.

The manifestation of AD is similar to asthma and allergic rhinitis, and is mainly related to local infiltration of T lymphocytes secreting interleukin-4 (IL-4), interleukin-13 (IL-13), etc. IL-4 and IL-13 are related to the development of the phenotype of regulatory helper T cells 2 (Th2), and can lead to overproduction of immunoglobulin (Ig) and increase of eosinophils. At the same time, increased levels of total IgE and allergen-specific IgE are also a feature of AD. At least 50% of AD patients have this feature, and the IgE is mainly for external environmental allergens.

Therefore, there are multiple abnormal immune response links in the occurrence and development of AD, such as presentation of Langerhans cells and skin dendritic cells to allergens, Th2-based abnormal immune response, regulatory T cell dysfunction, overproduction of IgE and elevated eosinophils.

The pathogenesis of AD is closely related to genetic and environmental factors, but the real cause of the pathogenesis of AD is still unclear. About 60% of AD patients may have a family history of atopic allergies. If one parent has the constitution of atopic allergy, there is a 60% chance that the child will have atopic allergies. In addition to genetic factors, the immune factors that need to be considered in the etiology of AD are: food allergies, allergies induced by exposure to allergens and irritants, allergies induced by aeroallergens, and immune regulation abnormalities.

At the present stage, there is no therapeutic drug with clear curative effect for AD. Therefore, at present, the symptoms of AD are mainly relieved by topical drugs such as glucocorticoid drugs, calcineurin inhibitors, topical antimicrobial agents, antihistamines and anti-inflammatory mediator drugs, immunosuppressants, etc.

However, the drugs have major adverse reactions, and most patients have concerns about hormone drugs. These not only bring great difficulties to the treatment of AD, but also bring great distress to patients' lives. In addition, these drugs are poorly tolerated by individual patients.

Therefore, there is still a need for a drug or treatment method that will not cause side effects to patients, can also be used to combat the onset of allergies and the development of skin inflammation, and relieve the symptoms of itching and eczema in patients, and can also be applied to various types of patients and has good tolerance to patients.

SUMMARY

The disclosure discloses *Bifidobacterium longum* CCFM1029. The *Bifidobacterium longum* CCFM1029 was deposited at the Guangdong Microbial Culture Collection Center on Oct. 11, 2018, with the accession number of GDMCC No. 60461, and the deposit address of $5^{th}$ Floor, Building No. 59, Courtyard No. 100, Xianlie Middle Road, Guangzhou. The *Bifidobacterium longum* CCFM1029 has the effects of relieving atopic dermatitis, and the effects are specifically embodied in:

(1) significantly improving the degree of ear swelling in mice with atopic dermatitis;
(2) significantly improving skin pathological symptoms and inflammatory cell infiltration in mice with atopic dermatitis;
(3) significantly reducing the total IgE level in the serum of mice with atopic dermatitis by regulating the immune system in mice;
(4) being beneficial to reducing degranulation of mast cells in mice to significantly improve dermatitis inflammation in mice with atopic dermatitis;
(5) significantly reducing the levels of Th2 cell-related cytokines (IL-4, IL-13) in local tissues of mice to restore the immune balance between Th1/Th2 in the local tissues of mice with atopic dermatitis; and
(6) significantly reducing the release of histamine in the local tissues of mice, alleviating skin itching symptoms in mice with atopic dermatitis, and thereby relieving dermatitis inflammation in the mice with atopic dermatitis.

The *Bifidobacterium longum* CCFM1029 was isolated from healthy human feces samples from Hangzhou, Zhejiang Province. The strain was sequenced and analyzed, and the 16S rRNA sequence of the strain is as shown in SEQ ID NO. 1. The sequence obtained by sequencing was subjected to nucleotide sequence alignment in NCBI, and the result showed that the strain was *Bifidobacterium longum*, named *Bifidobacterium longum* CCFM1029.

The convex surface of the *Bifidobacterium longum* CCFM1029 colony on an MRS medium is cushion-shaped, with complete edges, and is soft, moist, white and shiny.

The *Bifidobacterium longum* CCFM1029 can be used in preparation of products for prevention and/or treatment of atopic dermatitis. In the products, the viable count of the *Bifidobacterium longum* CCFM1029 is not less than $1 \times 10^6$ CFU/mL or $1 \times 10^6$ CFU/g.

The products include food, medicine or health care products. The medicine contains the *Bifidobacterium longum* CCFM1029, a drug carrier and/or pharmaceutical excipients. The food includes dairy products, soybean products, or fruit and vegetable products produced using a starter containing the *Bifidobacterium longum* CCFM1029; or the food includes solid beverages containing the *Bifidobacterium longum* CCFM1029.

The disclosure discloses a product for prevention and/or treatment of atopic dermatitis, and the product contains the *Bifidobacterium longum* CCFM1029. In the products, the viable count of the *Bifidobacterium longum* CCFM1029 is not less than $1 \times 10^6$ CFU/mL or $1 \times 10^6$ CFU/g.

The product includes food, medicine or health care products. The medicine contains the *Bifidobacterium longum* CCFM1029, a drug carrier and/or pharmaceutical excipients. The food includes dairy products, soybean products, or fruit and vegetable products produced using a starter containing the *Bifidobacterium longum* CCFM1029; or the food includes solid beverages containing the *Bifidobacterium longum* CCFM1029.

In one implementation of the disclosure, a preparation method of the starter is as follows: inoculating a culture medium with the *Bifidobacterium longum* CCFM1029 at an inoculum concentration of 2-4% of the total mass of the culture medium, and performing culturing at 37° C. for 18 h to obtain a culture solution; centrifuging the culture solution to obtain bacterial cells; washing the bacterial cells with a phosphate buffer with the pH of 7.2-7.4 for 3 times and then resuspending with a freeze-drying protective agent to obtain a resuspension; and freeze-drying the resuspension by a vacuum freezing process to obtain the starter. The mass ratio of the freeze-drying protective agent to the bacterial cells is 2:1. The culture medium comprises 87.7% water, 10% skim milk, 0.5% glucose, 1.5% tryptone, and 0.3% yeast extract solution, of the total mass of the culture medium. The pH of the culture medium is 6.8. The protective agent comprises 100 g/L skimmed milk powder, 150 g/L trehalose, and 10 g/L sodium L-glutamate.

The disclosure discloses *Bifidobacterium longum* CCFM1029. The *Bifidobacterium longum* CCFM1029 has the effects of relieving atopic dermatitis, and the effects are specifically embodied in:
(1) significantly improving the degree of ear swelling in mice with atopic dermatitis;
(2) significantly improving skin pathological symptoms and inflammatory cell infiltration in mice with atopic dermatitis;
(3) significantly reducing the total IgE level in the serum of mice with atopic dermatitis by regulating the immune system in mice;
(4) being beneficial to reducing degranulation of mast cells in mice to significantly improve dermatitis inflammation in mice with atopic dermatitis;
(5) significantly reducing the levels of Th2 cell-related cytokines (IL-4, IL-13) in local tissues of mice to restore the immune balance between Th1/Th2 in the local tissues of mice with atopic dermatitis; and
(6) significantly reducing the release of histamine in the local tissues of mice, alleviating skin itching symptoms in mice with atopic dermatitis, and thereby relieving dermatitis inflammation in the mice with atopic dermatitis.

Therefore, the *Bifidobacterium longum* CCFM1029 has great application prospects in the preparation of products (such as food, medicine or health care products) for the prevention and/or treatment of atopic dermatitis.

*Bifidobacterium longum* is a type of probiotics and has been included in the "Generally Recognized as Safe" list of US Food and Drug Administration. Therefore, the *Bifidobacterium longum* CCFM1029 screened by the disclosure is relatively healthy to the human body and has no side effects.

Figure 1:
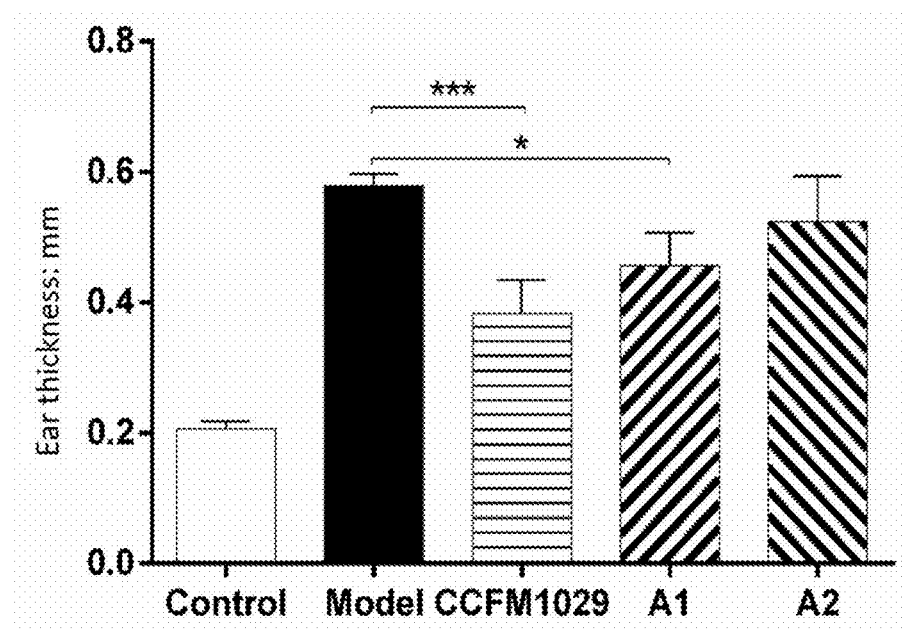
FIG. 1: Comparison of the effects of different groups in reducing ear thickness of mice with atopic dermatitis.

Among them, "*" indicates a significant difference from a Model group (P<0.05), and indicates an extremely significant difference from the Model group (P<0.01).

DETAILED DESCRIPTION

In the following examples, the skim milk was purchased from Brightdairy Co., Ltd., the glucose and yeast extract were purchased from Sinopharm Chemical Reagent Co., Ltd., the tryptone was purchased from OXOID, UK, and enzyme-linked immunosorbent assay kits were purchased from Nanjing SenBeiJia Biological Technology Co., Ltd.

The culture media involved in the following examples are as follows:

MRS solid culture medium (g/L): peptone 10 g/L, beef extract 10 g/L, glucose 20 g/L, sodium acetate 2 g/L, yeast powder 5 g/L, diammonium hydrogen citrate 2 g/L, $K_2PO_4 \cdot 3H_2O$ 2.6 g/L, $MgSO_4 \cdot 7 H_2O$ 0.1 g/L, $MnSO_4$ 0.05 g/L, Tween 80 1 mL/L, agar 20 g/L, and cysteine hydrochloride 0.5 g/L.

MRS liquid culture medium (g/L): peptone 10 g/L, beef extract 10 g/L, glucose 20 g/L, sodium acetate 2 g/L, yeast powder 5 g/L, diammonium hydrogen citrate 2 g/L, $K_2PO_4 \cdot 3H_2O$ 2.6 g/L, $MgSO_4 \cdot 7 H_2O$ 0.1 g/L, $MnSO_4$ 0.05 g/L, Tween 80 1 mL/L, and cysteine hydrochloride 0.5 g/L.

Example 1: Screening and Strain Identification of *Bifidobacterium longum*

1. Screening

Healthy human feces from Hangzhou, Zhejiang was taken as a sample. The sample was pretreated and stored in a refrigerator at −80° C. in about 20% glycerol. After the sample was taken out and thawed, the sample was mixed uniformly. 0.5 mL of the sample was pipetted and added to 4.5 mL, and the sample was subjected to gradient dilution with 0.9% normal saline containing 0.05% cysteine. An appropriate gradient dilution was selected and spread on an MRS solid culture medium added with 0.05% cysteine. The dilution was cultured at 37° C. for 48 h. Typical colonies were picked and streaked on an MRS solid culture medium for purification. A single colony was picked and transferred to an MRS liquid culture medium (containing 0.05% cysteine) for enrichment, and the bacteria were preserved with 30% glycerol to obtain a strain CCFM1029, a strain A1 and a strain A2.

2. Identification

The genomes of CCFM1029, A1 and A2 were extracted. The 16S rDNAs of CCFM1029, A1 and A2 were amplified and sequenced (by Invitrogen (Shanghai) Trading Co., Ltd., wherein the amplified nucleotide sequences of the 16S rDNAs of CCFM1029, A1 and A2 are shown in SEQ ID NO. 1, SEQ ID NO. 2 and SEQ ID NO. 3, respectively; the sequence of a forward primer 27F for strain identification is shown in SEQ ID NO. 4: 5'-AGAGTTT- GATCCTGGCTCAG-3'; and the sequence of a reverse primer 1492R is shown in SEQ ID NO. 5: 5'-GGT-TACCTTGTTACGACTT-3'). The sequences were subjected to nucleic acid sequence alignment in NCBI, and the results showed that the strains were *Bifidobacterium longum*, named *Bifidobacterium longum* CCFM1029, *Bifidobacterium longum* A1 and *Bifidobacterium longum* A2.

Example 2: Culture of *Bifidobacterium longum*

An MRS solid culture medium (containing 0.05% cysteine) was inoculated with the *Bifidobacterium longum* CCFM1029 and culturing was performed at 37° C. for 48 h. It was found that the convex surface of the colony was cushion-shaped, with complete edges, and is soft, moist, white and shiny, through observation of the colony.

An MRS liquid culture medium (containing 0.05% cysteine) was inoculated with the *Bifidobacterium longum* CCFM1029 and anaerobic culturing was performed at 37° C. for 24 h. The culture solution was transferred into a fresh MRS liquid culture medium (containing 0.05% cysteine) and cultured at same conditions for 24 h. Bacterial cells were centrifuged at 6000 g for 15 min, and then the bacterial cells were washed with 0.9% normal saline and recentrifuged at 6000 g for 10 min to obtain bacterial cells. The bacterial cells were resuspended with a 30% sucrose solution and cryopreserved at −80° C. for later use.

Example 3: Effects of Different *Bifidobacterium longum* on Ear Thickness of Mice with Atopic Dermatitis 50 healthy female C57BL/6 mice weighing 18-20 g were randomly divided into 5 groups, each with 10 mice. The 5 groups were respectively: a blank group (Control), a model group (Model) administered with 2,4-dinitrofluorobenzene (DNFB), a CCFM1029 group administered with *Bifidobacterium longum* CCFM1029, an A1 group administered with *Bifidobacterium longum* A1, and an A2 group administered with *Bifidobacterium longum* A2. The CCFM1029 group, the A1 group and the A2 group were all treatment groups.

The experiment lasts for four weeks in total. The first week was the adaptation period of mice. Gavage was started from the second week to the end of the experiment. The treatment groups were given bacterial solutions of the *Bifidobacterium longum* CCFM1029, A1 and A2 by gavage. 0.2 mL of bacterial solution (the total amount of viable bacteria in a single gavage was $1\times10^9$ CFU) was given per mouse per time by gavage. The blank group and the model group were not treated with the intervention of bacterial solutions, and only the same amount of normal saline was given by gavage as a control. The third to fourth weeks were the modeling period. On the $1^{st}$ day of modeling, 50 μL of 0.5% DNFB solution was applied to the right ears of the mice in the model group and the treatment groups to sensitize and stimulate skin lesions.

On the $5^{th}$, $8^{th}$, $11^{th}$, and $14^{th}$ days, 20 μL of 0.2% DNFB solution was applied to the right ears of the mice in the model group and the treatment groups. Only the same amount of acetone/olive oil matrix solution was applied to the right ears of the mice in the blank group as a control. All groups were free access to water and food.

Before modeling (that is, day 0), the ear thickness of the 5 groups of mice was measured with a digital spiral micrometer. After the modeling (that is, on the $15^{th}$ day), blood was taken and the mice were sacrificed. Then the ear thickness of the mice was measured immediately. The test results are shown in FIG. 1.

It can be seen from FIG. 1 that both the *Bifidobacterium longum* CCFM1029 and the *Bifidobacterium longum* A1 can significantly reduce the ear thickness of mice with atopic dermatitis and relieve the degree of ear swelling of the mice; while the *Bifidobacterium longum* A2 has no obvious relieving effect.

The experimental results show that the *Bifidobacterium longum* CCFM1029 has the effect of relieving the thickness and degree of swelling of the ears of mice with atopic dermatitis.

Example 4: Effects of Different *Bifidobacterium longum* on Skin Pathological Symptoms in Mice with Atopic Dermatitis 50 healthy female C57BL/6 mice weighing 18-20 g were randomly divided into 5 groups, each with 10 mice. The 5 groups were respectively: a blank group (Control), a model group (Model) administered with 2,4-dinitrofluorobenzene (DNFB), a CCFM1029 group administered with *Bifidobacterium longum* CCFM1029, an A1 group administered with *Bifidobacterium longum* A1, and an A2 group administered with *Bifidobacterium longum* A2. The CCFM1029 group, the A1 group and the A2 group were all treatment groups.

The experiment lasts for four weeks in total. The first week was the adaptation period of mice. Gavage was started from the second week to the end of the experiment. The treatment groups were given bacterial solutions of the *Bifidobacterium longum* CCFM1029, A1 and A2 by gavage. 0.2 mL of bacterial solution (the total amount of viable bacteria in a single gavage was $1\times10^9$ CFU) was given per mouse per time by gavage. The blank group and the model group were not treated with the intervention of bacterial solutions, and only the same amount of normal saline was given by gavage as a control. The third to fourth weeks were the modeling period. On the $1^{st}$ day of modeling, the back skin of the 5 groups of mice was depilated for an area of approximately 2.5 cm×2.5 cm, and 50 μL of 0.5% DNFB solution was applied to the depilated areas on the back of the mice in the model group and the treatment groups to sensitize and stimulate skin lesions. On the $5^{th}$, $8^{th}$, $11^{th}$, and $14^{th}$ days, 20 μL of 0.2% DNFB solution was applied to the depilated areas on the back of the mice in the model group and the treatment groups. Only the same amount of acetone/olive oil matrix solution was applied to the depilated areas on the back of the mice in the blank group as a control. All groups were free access to water and food.

After the modeling (that is, on the $15^{th}$ day), blood was taken and the mice were sacrificed. The skin of the depilated areas on the back of the mice was taken for histopathological analysis. Histopathological sections of the back skin of mice were subjected to hematoxylin-eosin staining, and then histopathological scoring was performed by professional technicians (the results are shown in FIG. 2).

Figure 2:
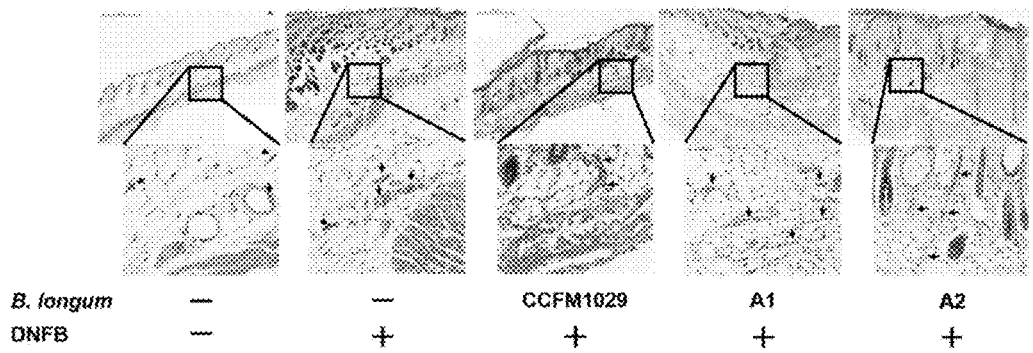
FIG. 2: Comparison of the effects of different groups in relieving skin pathological symptoms in mice with atopic dermatitis.

It can be seen from FIG. 2 that the structure of the epidermal cells on the back of mice in the blank group (Control) was normal, and there was no inflammation in all layers of the epidermis. The pathology of the skin lesions on the back of mice in the model group (Model) shows obvious inflammatory and proliferative changes and infiltration of lymphocytes and plasma cells, and the back skin was eroded and had proliferation of fibrous tissue. The structure of the epidermal cells on the back of mice in the *Bifidobacterium longum* CCFM1029 treatment group was almost normal, and there was no serious inflammation in all layers of the epidermis. There is obvious proliferation of fibrous tissue and relatively small amount of inflammation in the *Bifidobacterium longum* A1 and *Bifidobacterium longum* A2 treatment groups, and the pathological symptoms of atopic dermatitis in the skin of mice were relieved. The structure of epidermal cells in the remaining groups was obviously incomplete, and it was speculated that the skin was ulcerated and crusted, and had severe inflammation.

The experiment shows that the *Bifidobacterium longum* CCFM1029 can significantly improve skin inflammation in mice with atopic dermatitis.

Example 5: Effects of Different *Bifidobacterium longum* on Eosinophil Infiltration in Mice with Atopic Dermatitis 50 healthy female C57BL/6 mice weighing 18-20 g were randomly divided into 5 groups, each with 10 mice. The 5 groups were respectively: a blank group (Control), a model group (Model) administered with 2,4-dinitrofluorobenzene (DNFB), a CCFM1029 group administered with *Bifidobacterium longum* CCFM1029, an A1 group administered with *Bifidobacterium longum* A1, and an A2 group administered with *Bifidobacterium longum* A2. The CCFM1029 group, the A1 group and the A2 group were all treatment groups.

The experiment lasts for four weeks in total. The first week was the adaptation period of mice. Gavage was started from the second week to the end of the experiment. The treatment groups were given bacterial solutions of the *Bifidobacterium longum* CCFM1029, A1 and A2 by gavage. 0.2 mL of bacterial solution (the total amount of viable bacteria in a single gavage was $1 \times 10^9$ CFU) was given per mouse per time by gavage. The blank group and the model group were not treated with the intervention of bacterial solutions, and only the same amount of normal saline was given by gavage as a control. The third to fourth weeks were the modeling period. On the $1^{st}$ day of modeling, the back skin of the 5 groups of mice was depilated for an area of approximately 2.5 cm×2.5 cm, and 50 μL of 0.5% DNFB solution was applied to the depilated areas on the back of the mice in the model group and the treatment groups to sensitize and stimulate skin lesions. On the $5^{th}$, $8^{th}$, $11^{th}$, and $14^{th}$ days, 20 μL of 0.2% DNFB solution was applied to the depilated areas on the back of the mice in the model group and the treatment groups. Only the same amount of acetone/olive oil matrix solution was applied to the depilated areas on the back of the mice in the blank group as a control. All groups were free access to water and food.

After the modeling (that is, on the $15^{th}$ day), blood was taken and the mice were sacrificed. The skin of the depilated areas on the back of the mice was taken for histopathological analysis. Histopathological sections of the back skin of mice were subjected to hematoxylin-eosin staining, and then eosinophil counting and analysis were performed by professional technicians (the results are shown in FIG. 3).

Figure 3:
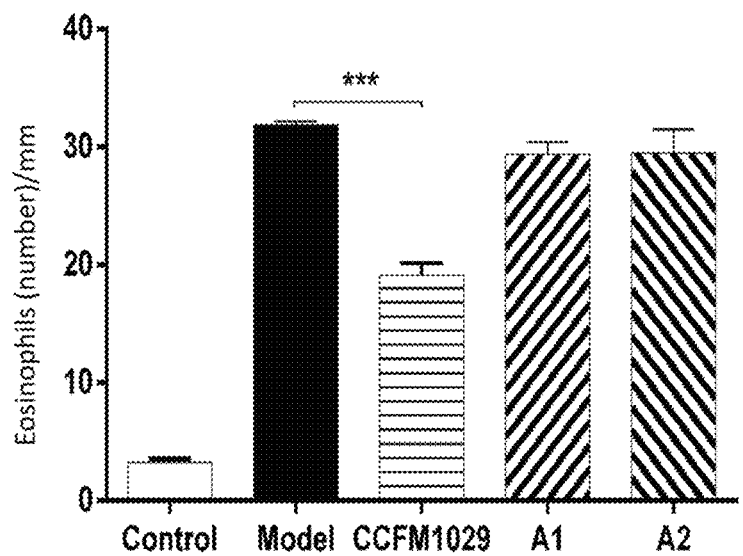
FIG. 3: Comparison of the effects of different groups in reducing skin eosinophil infiltration in mice with atopic dermatitis.

It can be seen from FIG. 3 that the *Bifidobacterium longum* CCFM1029 significantly reduced the number of eosinophils in the skin tissues, reduced the inflammatory infiltration produced by the eosinophils, and thereby inhibited skin tissue inflammation. However, the *Bifidobacterium longum* A1 group and *Bifidobacterium longum* A2 group cannot inhibit the number of eosinophils in the tissues, has no significant effect on tissue inflammatory infiltration, and cannot relieve skin inflammation in mice.

The experiment shows that the *Bifidobacterium longum* CCFM1029 can significantly inhibit the inflammatory infiltration produced by eosinophils in the skin of mice with atopic dermatitis.

Example 6: Effects of Different *Bifidobacterium longum* on the Total Serum IgE Level in Mice with Atopic Dermatitis 50 healthy female C57BL/6 mice weighing 18-20 g were randomly divided into 5 groups, each with 10 mice. The 5 groups were respectively: a blank group (Control), a model group (Model) administered with 2,4-dinitrofluorobenzene (DNFB), a CCFM1029 group administered with *Bifidobacterium longum* CCFM1029, an A1 group administered with *Bifidobacterium longum* A1, and an A2 group administered with *Bifidobacterium longum* A2. The CCFM1029 group, the A1 group and the A2 group were all treatment groups.

The experiment lasts for four weeks in total. The first week was the adaptation period of mice. Gavage was started from the second week to the end of the experiment. The treatment groups were given bacterial solutions of the *Bifidobacterium longum* CCFM1029, A1 and A2 by gavage. 0.2 mL of bacterial solution (the total amount of viable bacteria in a single gavage was $1 \times 10^9$ CFU) was given per mouse per time by gavage. The blank group and the model group were not treated with the intervention of bacterial solutions, and only the same amount of normal saline was given by gavage as a control. The third to fourth weeks were the modeling period. On the $1^{st}$ day of modeling, the back skin of the 5 groups of mice was depilated for an area of approximately 2.5 cm×2.5 cm, and 50 μL of 0.5% DNFB solution was applied to the depilated areas on the back of the mice in the model group and the treatment groups to sensitize and stimulate skin lesions. On the $5^{th}$, $8^{th}$, $11^{th}$, and $14^{th}$ days, 20 μL of 0.2% DNFB solution was applied to the depilated areas on the back of the mice in the model group and the treatment groups. Only the same amount of acetone/olive oil matrix solution was applied to the depilated areas on the back of the mice in the blank group as a control. All groups were free access to water and food.

After the modeling (that is, on the $15^{th}$ day), blood was taken and the mice were sacrificed. The serum of mice was taken, and the total serum IgE level was measured with an enzyme-linked immunosorbent assay kit (the results are shown in FIG. 4).

Figure 4:
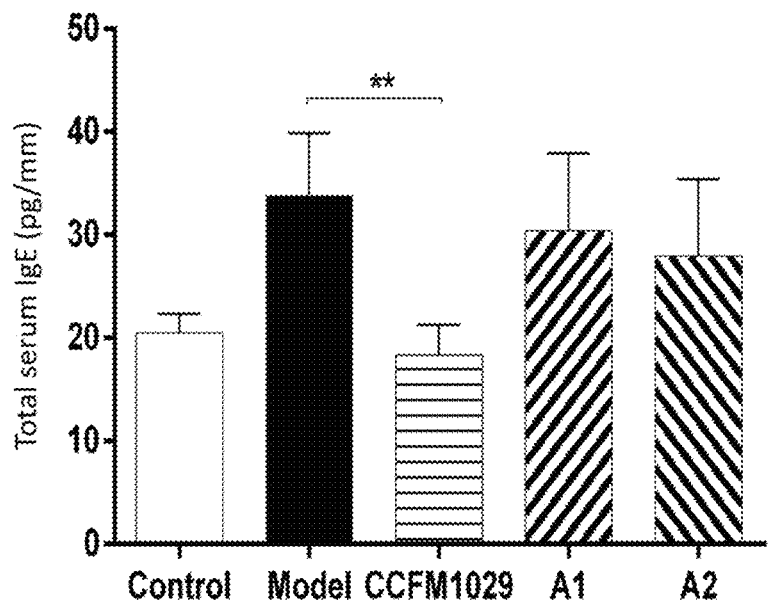
FIG. 4: Comparison of the effects of different groups in reducing the total serum IgE level in mice with atopic dermatitis.

It can be seen from FIG. 4 that compared with the model group (Model), the *Bifidobacterium longum* CCFM1029 significantly reduced the total serum IgE level in mice, and was beneficial to inhibiting the Th2-type immune response, thereby helping relieve the pathological inflammation of atopic dermatitis. However, the *Bifidobacterium longum* A1 group and the *Bifidobacterium longum* A2 group cannot inhibit the synthesis of serum IgE, so the intervention of the *Bifidobacterium longum* A1 and A2 has no significant effect on the pathological inflammation of atopic dermatitis.

The experiment shows that the *Bifidobacterium longum* CCFM1029 can significantly reduce the total serum IgE level in mice, and is beneficial to relieving the pathological inflammation of atopic dermatitis.

Example 7: Effects of Different *Bifidobacterium longum* on the Levels of IL-4 and IL-13 in the Skin Tissues of Mice with Atopic Dermatitis 50 healthy female C57BL/6 mice weighing 18-20 g were randomly divided into 5 groups, each with 10 mice. The 5 groups were respectively: a blank group (Control), a model group (Model) administered with 2,4-dinitrofluorobenzene (DNFB), a CCFM1029 group administered with *Bifidobacterium longum* CCFM1029, an A1 group administered with *Bifidobacterium longum* A1, and an A2 group administered with *Bifidobacterium longum* A2. The CCFM1029 group, the A1 group and the A2 group were all treatment groups.

The experiment lasts for four weeks in total. The first week was the adaptation period of mice. Gavage was started from the second week to the end of the experiment. The treatment groups were given bacterial solutions of the *Bifidobacterium longum* CCFM1029, A1 and A2 by gavage. 0.2 mL of bacterial solution (the total amount of viable bacteria in a single gavage was $1\times10^9$ CFU) was given per mouse per time by gavage. The blank group and the model group were not treated with the intervention of bacterial solutions, and only the same amount of normal saline was given by gavage as a control. The third to fourth weeks were the modeling period. On the $1^{st}$ day of modeling, the back skin of the 5 groups of mice was depilated for an area of approximately 2.5 cm×2.5 cm, and 50 μL of 0.5% DNFB solution was applied to the depilated areas on the back of the mice in the model group and the treatment groups to sensitize and stimulate skin lesions. On the $5^{th}$, $8^{th}$, $11^{th}$, and $14^{th}$ days, 20 μL of 0.2% DNFB solution was applied to the depilated areas on the back of the mice in the model group and the treatment groups. Only the same amount of acetone/olive oil matrix solution was applied to the depilated areas on the back of the mice in the blank group as a control. All groups were free access to water and food.

After the modeling (that is, on the $15^{th}$ day), blood was taken and the mice were sacrificed. Then the skin tissues of the depilated areas on the back of mice were taken, and the levels of Th2-type immune response cytokines IL-4 and IL-13 were measured with an enzyme-linked immunosorbent assay kit (the results are shown in FIG. 5 to FIG. 6).

Figure 5:
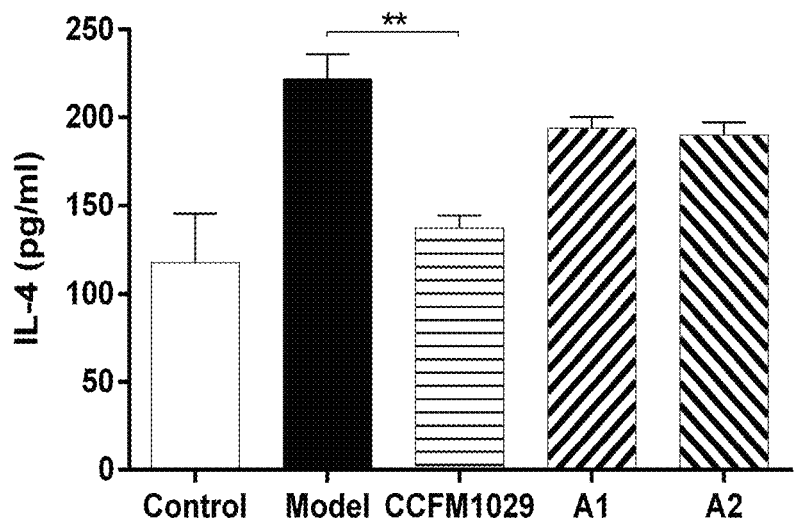
FIG. 5: Comparison of the effects of different groups in reducing the IL-4 level in the skin tissues of mice with atopic dermatitis.
Figure 6:
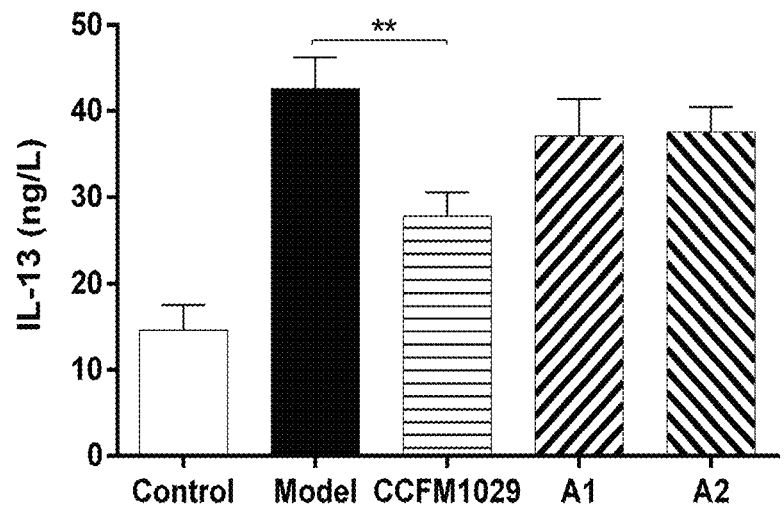
FIG. 6: Comparison of the effects of different groups in reducing the IL-13 level in the skin tissues of mice with atopic dermatitis.

It can be seen from FIG. 5 to FIG. 6 that compared with the model group (Model), the *Bifidobacterium longum* CCFM1029 significantly reduced the levels of IL-4 and IL-13 in the skin tissues of mice, and significantly inhibited the Th2-type immune response, thereby helping relieve the pathological inflammation state caused by Th2-type abnormal immune response.

However, the *Bifidobacterium longum* A1 group and the *Bifidobacterium longum* A2 group cannot reduce the levels of IL-4 and IL-13 in the skin tissues, so the intervention of the *Bifidobacterium longum* A1 and A2 has no significant effect on the pathological inflammation of atopic dermatitis.

The experiment shows that the *Bifidobacterium longum* CCFM1029 can significantly reduce the levels of cytokines IL-4 and IL-13 related to Th2-type immune response, and help relieve the pathological inflammation state caused by the Th2-type abnormal immune response.

Example 8: Effects of Different *Bifidobacterium longum* on the Level of Histamine in the Skin Tissues of Mice with Atopic Dermatitis 50 healthy female C57BL/6 mice weighing 18-20 g were randomly divided into 5 groups, each with 10 mice. The 5 groups were respectively: a blank group (Control), a model group (Model) administered with 2,4-dinitrofluorobenzene (DNFB), a CCFM1029 group administered with *Bifidobacterium longum* CCFM1029, an A1 group administered with *Bifidobacterium longum* A1, and an A2 group administered with *Bifidobacterium longum* A2. The CCFM1029 group, the A1 group and the A2 group were all treatment groups.

The experiment lasts for four weeks in total. The first week was the adaptation period of mice. Gavage was started from the second week to the end of the experiment. The treatment groups were given bacterial solutions of the *Bifidobacterium longum* CCFM1029, A1 and A2 by gavage. 0.2 mL of bacterial solution (the total amount of viable bacteria in a single gavage was $1\times10^9$ CFU) was given per mouse per time by gavage. The blank group and the model group were not treated with the intervention of bacterial solutions, and only the same amount of normal saline was given by gavage as a control. The third to fourth weeks were the modeling period. On the $1^{st}$ day of modeling, the back skin of the 5 groups of mice was depilated for an area of approximately 2.5 cm×2.5 cm, and 50 μL of 0.5% DNFB solution was applied to the depilated areas on the back of the mice in the model group and the treatment groups to sensitize and stimulate skin lesions. On the $5^{th}$, $8^{th}$, $11^{th}$, and $14^{th}$ days, 20 μL of 0.2% DNFB solution was applied to the depilated areas on the back of the mice in the model group and the treatment groups. Only the same amount of acetone/olive oil matrix solution was applied to the depilated areas on the back of the mice in the blank group as a control. All groups were free access to water and food.

After the modeling (that is, on the $15^{th}$ day), blood was taken and the mice were sacrificed. Then the skin tissues of the depilated areas on the back of mice were taken, and the inflammatory factor histamine related to degranulation of mast cells was measured with an enzyme-linked immunosorbent assay kit (the results are shown in FIG. 7).

Figure 7:
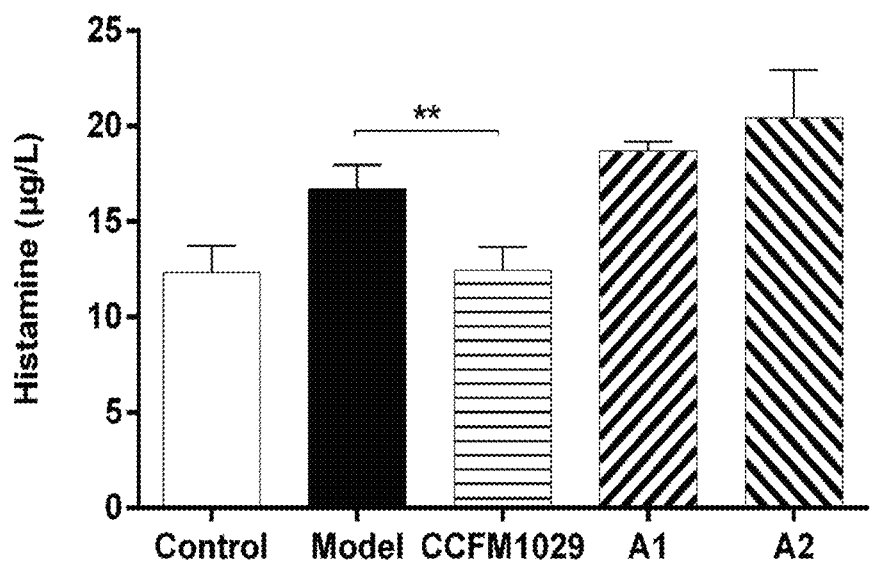
FIG. 7: Comparison of the effects of different groups in reducing the level of histamine in the skin tissues of mice with atopic dermatitis.

It can be seen from FIG. 7 that compared with the model group (Model), the *Bifidobacterium longum* CCFM1029 significantly reduced the level of histamine in the skin tissues of mice. It can be inferred that the *Bifidobacterium longum* CCFM1029 significantly reduced the degranulation of mast cells, prevented the release of histamine in the damaged skin tissues, and relieved skin itching of mice. However, the *Bifidobacterium longum* A1 group and the *Bifidobacterium longum* A2 group cannot reduce the level of histamine in the skin tissues, and even promotes the release of histamine. Therefore, the *Bifidobacterium longum* A1 group and the *Bifidobacterium longum* A2 group cannot inhibit degranulation of mast cells in the tissues or further prevent the release of histamine, and cannot relieve skin itching of the mice.

The experiment shows that the *Bifidobacterium longum* CCFM1029 can significantly reduce the level of histamine in skin tissues, and inhibit the degranulation of mast cells in skin tissues, thereby relieving skin itching of mice and preventing further development of atopic dermatitis.

Example 9: Preparation of Solid Beverage Containing *Bifidobacterium longum* CCFM1029

A culture medium was inoculated with the *Bifidobacterium longum* CCFM1029 at an inoculum concentration of 3% of the total mass of the culture medium and culturing was performed at 37° C. for 18 h to obtain a culture solution. The culture solution was centrifuged to obtain bacterial cells. The bacterial cells were washed with a phosphate buffer with the pH of 7.2-7.4 for 3 times, and then resuspended with a trehalose freeze-drying protective agent with the trehalose concentration of 100 g/L (the mass ratio of the freeze-drying protective agent to the bacterial cells was 2:1) to obtain a resuspension. The resuspension was freeze-dried by a vacuum freezing process to obtain *Bifidobacterium longum* CCFM1029 bacterial powder. The culture medium includes 87.7% water, 10% enzymatically hydrolyzed skim milk, 0.5% glucose, 1.5% tryptone and 0.3% yeast extract solution, of the total mass of the culture medium. The pH of the culture medium was 6.8.

The *Bifidobacterium longum* CCFM1029 bacterial powder containing 1×10^10 CFU was mixed with maltodextrin with the total mass of the bacterial powder and the maltodextrin being 1 gram to obtain a solid beverage containing the *Bifidobacterium longum* CCFM1029.

10 grams of the solid beverage containing the *Bifidobacterium longum* CCFM1029 was reconstituted with normal saline and the volume was set to 20 mL. 0.2 mL of the dilution was given to each mouse per day by gavage for three consecutive weeks. The solid beverage can effectively relieve the symptoms of atopic dermatitis in mice, and has excellent effects in the prevention and/or treatment of atopic dermatitis.

What is claimed is:

1. A composition, consisting of *Bifidobacterium longum* deposited at the Guangdong Microbial Culture Collection Center on Oct. 11, 2018, under accession number of GDMCC No. 60461 a phosphate buffer, and a freeze-drying protective agent, wherein the composition is freeze-dried.

2. The composition of claim 1, wherein viable count of the *B. longum* is not less than $1 \times 10^6$ CFU/mL or $1 \times 10^6$ CFU/g.

3. The product of claim 1, wherein the product further comprises a drug carrier and/or pharmaceutical excipients.

4. A method of treating atopic dermatitis, wherein the method comprises:

providing the composition of claim 1, administering by gavage a pharmaceutically effective dose of the composition to a subject in need thereof, thereby treating atopic dermatitis in the subject.

5. The method of claim 4, wherein the viable count of the *Bifidobacterium longum* is not less than $1 \times 10^6$ CFU/mL or $1 \times 10^6$ CFU/g.

6. The method of claim 5, wherein the composition comprises food, medicine, or health care products.

7. The method of claim 6, wherein the medicine further comprises a drug carrier and/or pharmaceutical excipients.

8. The method of claim 6, wherein the food comprises dairy products, soybean products, fruit products, or vegetable products, produced using a starter comprising the *B. longum*.

9. A process for producing the composition of claim 1, beginning with a starter, which is produced as follows:
   inoculating a culture medium with the *B. longum* at an inoculum concentration of 2% to 4% of the total mass of the culture medium, and
   culturing at 37° C. for 18 hours to obtain a culture solution;
   centrifuging the culture solution to obtain bacterial cells;
   washing the bacterial cells with a phosphate buffer with the pH of 7.2 to 7.4 for 3 times and then resuspending with a freeze-drying protective agent to obtain a resuspension; and
   freeze-drying the resuspension by a vacuum freezing process to obtain the starter.

10. The process of claim 9, wherein the mass ratio of the freeze-drying protective agent to the bacterial cells is 2:1.

11. The process of claim 9, wherein the culture medium comprises 87.7% water, 10% skim milk, 0.5% glucose, 1.5% tryptone, and 0.3% yeast extract solution, of the total mass of the culture medium.

12. The process of claim 9, wherein the pH of the culture medium is 6.8.

13. The process of claim 9, wherein the freeze-drying protective agent comprises 100 g/L skimmed milk powder, 150 g/L trehalose, and 10 g/L sodium L-glutamate.

* * * * *

SEQUENCE LISTING

<160> NUMBER OF SEQ ID NOS: 5

<210> SEQ ID NO 1
<211> LENGTH: 464
<212> TYPE: DNA
<213> ORGANISM: Artificial Sequence
<220> FEATURE:
<223> OTHER INFORMATION: Synthetic DNA

<400> SEQUENCE: 1

```
gttctgcaga gcggagcggg tcaccttgac cgggtcggtc acaccggcgg ccagcaggtc     60
ttcgtaggtg tcggtggcgg cgttgaagcc ttcgccatca ggcagggagc ggacggtgtt    120
gatgaccacg tcaccggaca cgccggcgtt ctcggcgatc tgcttgatcg gggcctcgat    180
ggcgcggaac acgatggcgg caccggtagc ctcttcgccg gtcagggagg tgacggcctc    240
ggtcttctcg gccttggcag cagcctgaac gagggccacg ccaccgccgg gcagcaggcc    300
ttcctcgatg gcggccttgg cgttacgcac ggcatcttcg atgcggtgct tgcgctcctt    360
ggcctcgacc tcggtggcag cgccgacctt gatgacagcc acgccgccag ccagcttggc    420
cagacgctcc tgcagcttct cacgacgtta aatcaggaaa agtt                     464
```

<210> SEQ ID NO 2
<211> LENGTH: 877
<212> TYPE: DNA
<213> ORGANISM: Artificial Sequence
<220> FEATURE:
<223> OTHER INFORMATION: Synthetic DNA

<400> SEQUENCE: 2

```
gggatggggg gttgctttac aatgcaagtc gtacgggatc catcaggctt tgcttggtgg     60
tgagagtggc gaacgggtga gtaatgcgtg accgacctgc cccatacacc ggaatagctc    120
ctggaaacgg gtggtaatgc cggatgctcc agttgatcgc atggtcttct gggaaagctt    180
tcgcggtatg ggatggggtc gcgtcctatc agcttgacgg cggggtaacg gcccaccgtg    240
gcttcgacgg gtagccggcc tgagagggcg accggccaca ttgggactga gatacggccc    300
agactcctac gggaggcagc agtggggaat attgcacaat gggcgcaagc ctgatgcagc    360
gacgccgcgt gagggatgga ggccttcggg ttgtaaacct cttttatcgg ggagcaagcg    420
agagtgagtt tacccgttga ataagcaccg gctaactacg tgccagcagc cgcggtaata    480
cgtagggtgc aagcgttatc cggaattatt gggcgtaaag ggctcgtagg cggttcgtcg    540
cgtccggtgt gaaagtccat cgcttaacgg tggatccgcg ccgggtacgg gcgggcttga    600
gtgcggtagg ggagactgga attcccggtg taacggtgga atgtgtagat atcgggaaga    660
acaccaatgg cgaaggcagg tctctgggcc gttactgacg ctgaggagcg aaagcgtggg    720
gagcgaacag gattagatac cctggtagtc cacgccgtaa acggtggatg ctggatgtgg    780
ggcccgttcc acgggttccg tgtcggagct aacgcgttaa gcatcccgcc tggggagtac    840
ggccgcaagg ctaaaactca aagaaattga cggggc                              877
```

```
<210> SEQ ID NO 3
<211> LENGTH: 872
<212> TYPE: DNA
<213> ORGANISM: Artificial Sequence
<220> FEATURE:
<223> OTHER INFORMATION: Synthetic DNA

<400> SEQUENCE: 3
gggattgcgg ctgcttacca tgcaagtcga cgggatccat caagcttgct tggtggtgag      60
agtggcgaac gggtgagtaa tgcgtgaccg acctgcccca tacaccggaa tagctcctgg     120
aaacgggtgg taatgccgga tgctccagtt gatcgcatgg tcttctggga aagctttcgc     180
ggtatgggat ggggtcgcgt cctatcagct tgacggcggg gtaacggccc accgtggctt     240
cgacgggtag ccggcctgag agggcgaccg gccacattgg gactgagata cggcccagac     300
tcctacggga ggcagcagtg gggaatattg cacaatgggc gcaagcctga tgcagcgacg     360
ccgcgtgagg gatggaggcc ttcgggttgt aaacctcttt tatcggggag caagcgagag     420
tgagtttacc cgttgaataa gcaccggcta actacgtgcc agcagccgcg gtaatacgta     480
gggtgcaagc gttatccgga attattgggc gtaaagggct cgtaggcggt tcgtcgcgtc     540
cggtgtgaaa gtccatcgct taacggtgga tccgcgccgg gtacgggcgg gcttgagtgc     600
ggtaggggag actggaattc ccggtgtaac ggtggaatgt gtagatatcg ggaagaacac     660
caatggcgaa ggcaggtctc tgggccgtta ctgacgctga ggagcgaaag cgtggggagc     720
gaacaggatt agataccctg gtagtccacg ccgtaaacgg tggatgctgg atgtggggcc     780
cgttccacgg gttccgtgtc ggagctaacg cgttaagcat cccgcctggg gagtacggcc     840
gcaaggctaa aactcaaaga aattgacggg gg                                   872

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
agagtttgat cctggctcag                                                  20

<210> SEQ ID NO 5
<211> LENGTH: 19
<212> TYPE: DNA
<213> ORGANISM: Artificial Sequence
<220> FEATURE:
<223> OTHER INFORMATION: Synthetic DNA

<400> SEQUENCE: 5
ggttaccttg ttacgactt                                                   19
```